(12) United States Patent
Cummins et al.

(10) Patent No.: US 8,691,285 B2
(45) Date of Patent: *Apr. 8, 2014

(54) ANTI-MICROBIAL APPLICATIONS FOR ACIDIC COMPOSITION OF MATTER

(75) Inventors: Barry Cummins, Butler, KY (US); David Creasey, Splendora, TX (US)

(73) Assignee: CMS Innovative Technologies, Inc., Danbury, CT (US)

( * ) Notice: Subject to any disclaimer, the term of this patent is extended or adjusted under 35 U.S.C. 154(b) by 57 days.

This patent is subject to a terminal disclaimer.

(21) Appl. No.: 13/182,481

(22) Filed: Jul. 14, 2011

(65) Prior Publication Data

US 2012/0027869 A1 Feb. 2, 2012

Related U.S. Application Data

(63) Continuation-in-part of application No. 11/293,535, filed on Dec. 2, 2005, now Pat. No. 8,012,511, which is a continuation-in-part of application No. 10/453,805, filed on Jun. 3, 2003, now Pat. No. Re. 41,109, which is an application for the reissue of Pat. No. 6,242,011, which is a continuation-in-part of application No. 08/611,764, filed on Mar. 8, 1996, now Pat. No. 5,989,595.

(51) Int. Cl.
| | |
|---|---|
| *A01N 59/00* | (2006.01) |
| *A01N 59/02* | (2006.01) |
| *A01N 59/06* | (2006.01) |
| *A01N 59/16* | (2006.01) |
| *A01N 59/20* | (2006.01) |
| *A01N 59/26* | (2006.01) |
| *A01N 37/02* | (2006.01) |
| *A01N 37/06* | (2006.01) |
| *C02F 1/76* | (2006.01) |

(52) U.S. Cl.
USPC ........... 424/601; 424/604; 424/606; 424/617; 424/618; 424/637; 424/638; 424/639; 424/641; 424/642; 424/665; 424/682; 424/697; 424/703; 424/709; 424/710; 424/713; 424/719; 424/720; 514/557; 514/574; 514/886; 514/887; 210/756

(58) Field of Classification Search
USPC ......... 424/604, 606, 617, 637–639, 641, 697, 424/703, 709, 710, 713, 719, 720, 601, 618, 424/642, 665, 682; 514/557, 574, 886, 887; 210/756

See application file for complete search history.

(56) References Cited

U.S. PATENT DOCUMENTS

| | | | |
|---|---|---|---|
| 6,242,011 B1 * | 6/2001 | Cummins | 424/710 |
| 6,565,893 B1 * | 5/2003 | Jones et al. | 424/616 |
| 7,192,618 B2 * | 3/2007 | Cummins et al. | 426/321 |
| RE41,109 E * | 2/2010 | Cummins | 424/710 |
| 8,012,511 B1 * | 9/2011 | Cummins et al. | 424/604 |

OTHER PUBLICATIONS

Block, S.S. Disinfection, Sterilization, and Preservation. 4th ed. Lea & Febiger, Philadelphia, pp. 722-723 (1991).*

* cited by examiner

*Primary Examiner* — John Pak
(74) *Attorney, Agent, or Firm* — McCarter & English

(57) ABSTRACT

Methods of using a non-irritant, low pH acidic composition to destroy undesirable microorganisms are described. The methods may be used on food products, food processing equipment, and in aqueous solutions.

15 Claims, 2 Drawing Sheets

ANTI-MICROBIAL APPLICATIONS FOR ACIDIC COMPOSITION OF MATTER

RELATED APPLICATIONS

This invention is a continuation-in-part of application Ser. No. 11/293,535, filed Dec. 2, 2005, now U.S. Pat. No. 8,012, 511, issued Sep. 6, 2011, which is a continuation-in-part of application Ser. No. 10/453,805, filed Jun. 3, 2003, now Pat. No. RE41,109, issued Feb. 9, 2010, which is a reissue of application Ser. No. 09/369,096, filed Aug. 5, 1999 and-issued as U.S. Pat. No. 6,242,011 on Jun. 5, 2001, which is a continuation-in-part of application Ser. No. 08/611,764, filed Mar. 8, 1996, now U.S. Pat. No. 5,989,595, issued Nov. 23, 1999. Each of these applications is incorporated, in their entirety, herein by reference.

FIELD OF THE INVENTION

This invention relates to methods of using a low pH composition of matter as a bactericide, fungicide, or viricide. The composition is suitable for destroying microorganisms on foods and food processing equipment.

BACKGROUND

The use of acids and acidic chemicals for killing deleterious organic organisms, such as bacteria, germs, and viruses is well known in the art. Chlorine and hydrochloric acid are especially useful as bactericides and are used universally as cleaning agents. Chlorine is also an effective viricide.

Bacteria play an important role in the deterioration of human foodstuffs. Foods such as fish are particularly susceptible to rapid deterioration, especially at room temperature, and compounds for the preservations of foods or the retardation of bacteria growth have been employed in the past. One of the problems with such compounds is that in certain increased levels, they can be toxic to human beings, thereby defeating the purpose of preserving the foodstuffs.

Because of the extremely acidic nature of some of the bactericides and viricides that have been utilized in the past, oftentimes they can cause skin irritation or other side effects for human begins coming in contact with these compositions, or can even be fatal if accidentally consumed. Chlorine has had other negative implications in terms of the environment, and is not environmentally friendly because of the release of chlorine gas into the environment.

SUMMARY OF THE INVENTION

Methods for destroying microorganisms on a food product, food processing equipment, or in an aqueous solution are described. The methods comprise applying to the food product, food processing equipment, or aqueous solution a composition that is not an irritant, prepared by the steps comprising a) combining a low pH acid of approximately 98% purity, selected from the group consisting of sulfuric acid, phosphoric acid, fumaric acid and acetic acid, with water and an ammonium compound or a metal sulfate to provide a mixture;

b) heating the mixture of step a) in a pressurized vessel at approximately 15 psi at a temperature in a range between 250° F. and 1200° F.;

c) cooling the mixture; and d) adding a stabilizer at 10 percent of the total weight of the mixture of step c) to the mixture after cooling, wherein the stabilizer comprises the mixture of step a).

A metal sulfate and/or chlorine may be further added to the composition. The composition may be diluted prior to use.

Figure 1:
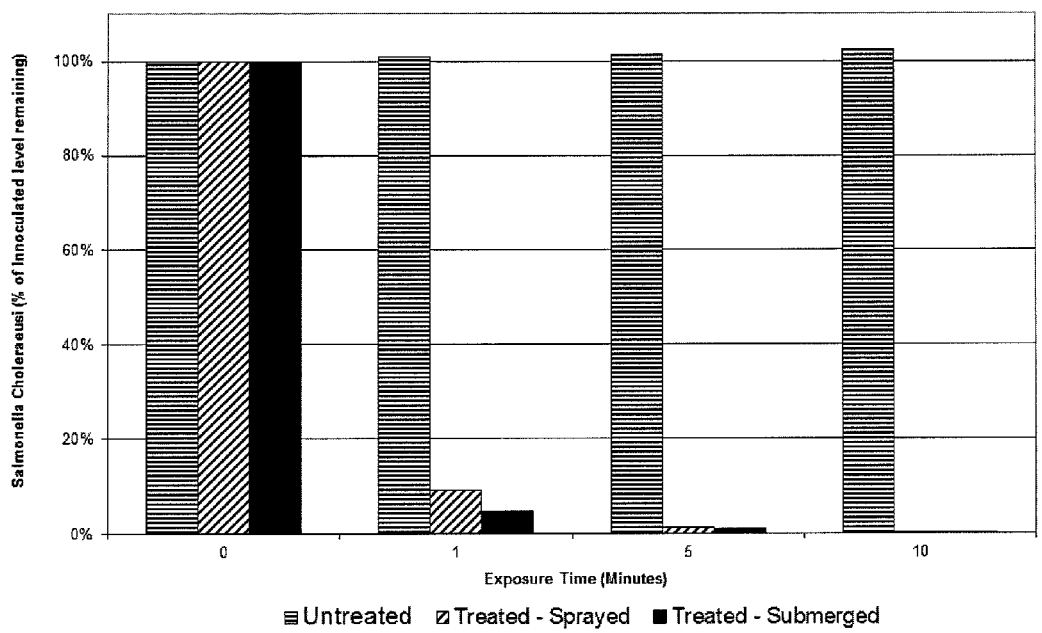
FIG. 1 is a graph showing the effects of the acidic composition described in Example 7 on the presence of *S. choleraesuis* in tomatoes.

DETAILED DESCRIPTION OF THE INVENTION

The present invention provides for a composition of matter and the method of making it that produces a composition that operates in a very low pH range to provide toxicity to bacteria, viruses, and certain malignant cells that attack human skin dermatologically, while at the time proving to be nontoxic to human beings and not harmful to healthy human cells.

In U.S. Pat. Nos. 5,989,595 and RE 41,109 to Cummins, an acidic composition of matter is disclosed that is useful for destroying microorganisms that spoil food, such as fish. The composition of matter, patented by Cummins, is expandable to include additional reactants that provide a very low pH composition that is nontoxic to human beings and not harmful to healthy human cells.

Headlines in 2005 regarding the avian flu in various countries and the threat of a global pandemic encourages consideration of the use of the acidic, non-toxic composition of the present invention to decrease the concentration of ammonia gases in open chicken pens. The ammonia gas, from chicken waste, acts as an irritant to the lungs of the fowl making them vulnerable to infection by the deadly virus that causes avian flu. The present invention can provide a two-fold benefit for chickens or fowl in open pens. First, by converting ammonia to a harmless salt, the free ammonia gas no longer irritates the lungs of penned birds; the birds will have a stronger immune system and will be less susceptible to the flu virus. Second, when ammonia is converted to a harmless salt, the feet pads of the birds or fowl will not have chemical ammonia burns causing the birds to become inactive and develop pneumonia from inactivity.

The composition of matter provided by the present invention forms a highly effective composition to kill or retard the growth of microorganisms, especially such as bacteria, viruses, and other microorganisms, and is compatible with use on food products and food processing equipment.

The first basic ingredient used is a low pH acid such as sulfuric acid, phosphoric acid, fumaric acid, acetic acid and stabilized hydrochloric acid, preferably of very high purity, between approximately 98 percent to approximately 99.9 percent purity. The acid is placed in a container at a predetermined quantity. The next step is to place water, preferably distilled, filtered, deionized, pharmaceutical or medical grade water in a separate container and heat said water to 140° F., at which time 2.77 lbs per gallon of 21 percent active metallic sulfate, or ammonium compound such as ammonium sulfate, is added to the water using a 316L stainless tube to inject air or a mechanical mixer to dissolve the ammonium compound in the water.

The resulting mixtures containing an ammonium compound or metallic sulfate are injected simultaneously at the same ratio into a large, stainless steel pressure vessel that is maintained at a pressure in a range between approximately 1 psi to approximately 20 psi above atmospheric pressure, preferably between approximately 2 psi and 7 psi above atmospheric pressure. The mixture is forced into the pressure vessel, which itself has positive and negative electrodes for passing a DC current through the mixture as it is filled into the pressure vessel. At least one amp of DC current is maintained approximately 1 ft above the base of the pressure vessel. Spargers, including spray head nozzle-like spargers, are used to force the mixture in a spray-in form into the pressure vessel.

The reaction of acid, water and ammonium compound or metallic sulfate is an exothermic reaction. The time and temperature of the reaction will vary based on the amount of reactants, size of reactor and reactivity of selected reactants. The temperature of the mixture is preferably maintained in a range between approximately 250° F. and approximately 1200° F., more preferably at approximately 300° F.-800° F. If the reaction temperatures are not reached the reaction mixture is not stable, there will be strong ammonia or sulfur odors. The reaction time varies between 60 minutes and 16 hours, preferably between 3 and 8 hours, more preferably between approximately 3 to 4 hours when reactants are preheated.

Preheating is recommended with smaller volumes of reactants, between approximately 400-1000 gallons. For example, it would be advantageous to preheat ammonium sulfate so that it stabilizes at approximately 160° F., and then preheat sulfuric acid by raising the temperature from ambient temperature to approximately 125° F. before mixing these reactants, then the reaction temperature is reached quickly and maintained for a shorter period of time, such as 3-4 hours. Volumes larger than 1000 gallons do not require preheating.

A cooling jacket is required to keep the temperature below approximately 1200° F. During this process, excess gas is removed, which is believed to be hydrogen gas. A separate gas distributor is mounted within the liquid in the form of perpendicular spargers that take air and inject it into the mixture during the heating process, which causes rotation of the fluid, creating a dynamic action in which the fluid is rotating about in the pressure vessel. After approximately 4 hours, the mixture is allowed to cool down to room temperature. At the end of the cool down period, another 10 percent of the total weight of the original mixture is added to the cooled down mixture to act as a stabilizer. The stabilizer can be added when the reaction mixture has a temperature between room temperature (approximately 70° F.) and approximately 160° F. The exact chemical formula for the resultant composition is not clearly known. Other components, such as metal ions and chlorine, may be added to the composition and the composition may be diluted prior to use.

As shown in Examples 4-8, metal sulfates, such as copper, silver, zinc, magnesium, and manganese, can be added to the acidic composition whether it is originally prepared with an ammonium compound or a metal sulfate. When the acidic composition is originally prepared with sodium sulfate instead of an ammonium compound, the composition is compatible with chlorine, as shown in Example 5.

The resulting combinations are very suitable for inhibiting growth of bacterial fungal, and viral pathogens on food products, such as fish, meat, poultry, and produce, food-processing materials, and aqueous solutions, such as water. Produce includes any edible part of a plant, e.g., roots, stems, leaves, fruits, seeds, and flowers, as well as edible fungi, e.g., mushrooms.

Before providing specific examples of reactants and the reaction process for making the acidic composition, the table below provides a list of a broad range of reactants that will form a low pH composition with equally effective results. Table I, can be used by a person with skill in the art to make a judicious selection of one reactant from column 1 or column 2, one reactant from column 3 and one reactant from column 4. These reactants would have a ratio within approximately ±25% to approximately ±45%, preferably within approximately 10% of the ratios discussed in the examples below. A person skilled in the art can make the appropriate adjustments within the ratios given based on the need for safety and stability of the finished product.

TABLE I

Reactants Useful in Preparing Low pH Acidic Composition

| Column 1<br>Urea or Ammonium<br>Compounds | Column 2<br>Metallic<br>Sulfates | Column3<br>Strong, Low pH<br>Acids | Column 4<br>Water |
|---|---|---|---|
| 46% urea substitute | sodium sulfate | sulfuric acid | distilled |
| anhydrous<br>ammonia | magnesium<br>sulfate | phosphoric acid | deionized |
| ammonium sulfate | zinc sulfate | fumaric acid | filtered |
| Ammonium nitrate<br>with buffers | manganese<br>sulfate | acetic acid | pharmaceutical<br>or medical<br>grade |
| | copper sulfate | | |

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

EXAMPLES

Example 1

The first ingredient used is sulfuric acid, preferably of around 98 percent purity. The sulfuric acid is placed in a container at a predetermined quantity. The next step is to place distilled water in a separate container and heat said water to 140° F., at which time 2.77 lbs per gallon of 21 percent active ammonium sulfate is added to the water using a 316 L stainless tube to inject air to dissolve the ammonium sulfate in the $H_2O$.

Simultaneously, the $H_2SO_4$, and the $H_2O$, and the ammonium sulfate $(NH_4)_2SO_4$ are injected into a large 400 gallon, stainless steel vessel that is maintained at 15 psi above atmospheric pressure through a plurality of sprayers (spargers).

Air under pressure is also introduced through sprayers in the bottom of the container, perpendicular to the liquid mixture, which forces the liquid mixture, which forces the liquid mixture to dynamically rotate within the pressure vessel.

Two electrodes, a cathode and anode, provide a DC voltage 1 ft above the bottom of the container at approximately 1 to 3 amps, with the electrodes being 3 ft apart.

The mixture is heated to a temperature not to exceed approximately 1200° F. and maintained at the temperature for 3 to 4 hours, during which time excess hydrogen gas is removed.

After 4 hours, the mixture is allowed to return and cool down to room temperature. After cool down, an additional 10 percent of the same mixture, is reintroduced into the original cool down mixture to act as a stabilizer. Other stabilizer can be substituted. The resulting composition can be used as is or diluted with distilled water as a fish preservative and applied to the skin of the fish. This would be fish at room temperature that can be preserved for weeks without refrigeration. The composition can also be added with effective dermatological creams, and without dilution to retard or destroy melanoma cancer cells on human skin.

Example 2

The composition as shown in Example 1 can be altered by the substitution of urea for the ammonium sulfate in the amount of 46 percent active urea. The remainder of the methodology will be the same.

It is believed that numerous applications as a bactericide, a fungicide, a viricide or other active acidic cleaning agent can be used for the compound at extremely low pHs (below 2), while at the same time the composition is not an irritant or deleterious to healthy human cells.

The following is an alternate embodiment of the invention.

The mixture shall consist of sulfuric acid, water and ammonium sulfate, or substitute 46 percent urea for the 21 percent ammonium sulfate.

One pound of 21 percent ammonium sulfate for gallon of water up to 5 pounds of 21 percent ammonium sulfate per gallon of water (distilled) with the ratio of water and ammonium sulfate to the sulfuric acid being from a 1 to 1 mixture up to a 5 to 1 mixture with the higher number being the water and ammonium sulfate mixture. Mixtures ratios are by weight.

Temperature ranges are from approximately 300° F. and not to exceed approximately 1200° F., preferably between approximately 350° F. and approximately 500° F. for consistency of the finished product. Pressures range from approximately 5 PSI to approximately 800 PSI and DC voltage ranges from approximately 1 amp to approximately 100 amps.

There are 4 things that affect the rate of reaction of the invention: temperature, pressure, amperage, and the amount of product being used. These are four variables that determine how long the process takes.

Example 3

Sulfuric acid, preferably around 98% purity, is placed in container in a predetermined quantity.

The next step is to place distilled water in a separate container and heat the water to approximately 140° F. at which time 2.77 pounds per gallon of 21 percent active ammonium sulfate is added to the water using a 316 L stainless tube to inject air to dissolve the ammonium sulfate in the water.

Simultaneously, the $H_2SO_4$, and the $H_2O$, and the ammonium sulfate $(NH_4)_2SO_4$ are injected into a large 400 gallon, stainless steel vessel that is maintained at 15 psi above atmospheric pressure through a plurality of sprayers (spargers).

Air under pressure is also introduced through sprayers in the bottom of the container, perpendicular to the liquid mixture, which forces the liquid mixture to dynamically rotate with the pressure vessel.

Two electrodes, a cathode and an anode provide a DC voltage one foot above the bottom of the container at approximately 3 amps with the electrodes being three feet apart.

The mixture is heated to 800° F. and maintained at that temperature for three to four hours during which time excess hydrogen gas is removed.

After four hours, the mixture is allowed to return and cool down to room temperature. After cool down, an additional lot of the same mixture, is reintroduced into the original cool down mixture to act as a stabilizer. The resulting composition can be used as is or diluted with distilled water as a fish preservative and applied to the skin of the fish.

Example 4

Using the same process as described in Example 3, phosphoric acid, preferably around 98% purity, is placed in a container in a predetermined quantity, such as approximately 1 gallon to approximately 2 gallon ratio with the water.

The next step is to place distilled water in a separate container and heat the water to approximately 140° F. at which time approximately 1 lb to approximately 3 lbs per gallon of sodium sulfate is added to the water using a mechanical mixer to dissolve the sodium sulfate in the water.

Simultaneously, the phosphoric acid, water, and the sodium sulfate $(Na_2SO_4)$ are injected into a large 400 gallon, stainless steel vessel that is maintained at 15 psi above atmospheric pressure through a plurality of sprayers (spargers).

Air under pressure is also introduced through sprayers in the bottom of the container, perpendicular to the liquid mixture, which forces the liquid mixture to dynamically rotate with the pressure vessel.

Two electrodes, a cathode and an anode provide a DC voltage one foot above the bottom of the container at approximately 3 amps with the electrodes being three feet apart.

The mixture is heated to approximately 350° F. and maintained at that temperature for three to four hours during which time excess hydrogen gas is removed.

After four hours, the mixture is allowed to cool down to room temperature. After cool down, an additional lot (10-15 weight percent) of the original mixture of acid, water and sodium sulfate, is reintroduced into the cooled reaction mixture to act as a stabilizer. The resulting composition can be used as is or diluted with distilled water for a spray or wash to be applied to fowl held in open pens.

Example 5

When the low pH acidic composition of the present invention is prepared (with electrolysis) in accordance with the procedure in Example 1 and sodium sulfate is substituted for ammonium sulfate, the resulting composition is very compatible with the use of chlorine solutions in the treatment of water and waste water. Also, when the use of direct current (DC) is omitted from the process of Example 1 (without electrolysis), the product with sodium sulfate is equally effective and compatible with processes using chlorine for water treatment. In Table II below, there are results of chlorine compatibility tests using the low pH acidic composition of the present invention, made with sodium sulfate, with and without electrolysis.

TABLE II

| Chlorine Compatibility Tests of Low pH Acidic Composition made with Sodium Sulfate | | | |
|---|---|---|---|
| Test #1 - 1 ppm Chlorine, 1 ppm copper (Acid, Water, Sodium Sulfate - w/electrolysis) | | | |
| Time (minutes) | Soln 1 (ppm) | Soln 2 (ppm) | |
| 0 | 1.08 | 1.08 | Starting FAC* |
| 15 | 1.09 | 1.09 | |
| 30 | 1.09 | 1.10 | |
| 45 | 1.08 | 1.08 | |
| 60 | 1.09 | 1.08 | No Reduction |

TABLE II-continued

Chlorine Compatibility Tests of Low pH Acidic
Composition made with Sodium Sulfate Test #2 - 2 ppm Chlorine, 1 ppm copper
(Acid, Water, Sodium Sulfate - w/electrolysis)

| Time (minutes) | Soln 1 (ppm) | Soln 2 (ppm) | |
|---|---|---|---|
| 0 | 1.99 | 1.99 | Starting FAC* |
| 15 | 2.00 | 2.02 | |
| 30 | 2.04 | 2.03 | |
| 45 | 2.03 | 2.02 | |
| 60 | 2.05 | 2.03 | No Reduction |

Test #3 - 1 ppm Chlorine, 1 ppm copper
(Acid, Water, Sodium Sulfate - No electrolysis)

| Time (minutes) | Soln 1 (ppm) | Soln 2 (ppm) | |
|---|---|---|---|
| 0 | 1.09 | 1.09 | Starting FAC* |
| 15 | 1.08 | 1.09 | |
| 30 | 1.07 | 1.08 | |
| 45 | 1.09 | 1.10 | |
| 60 | 1.09 | 1.11 | No Reduction |

Test #4 - 2 ppm Chlorine, 1 ppm copper
(Acid, Water, Sodium Sulfate - No electrolysis)

| Time (minutes) | Soln 1 (ppm) | Soln 2 (ppm) | |
|---|---|---|---|
| 0 | 2.01 | 2.00 | Starting FAC* |
| 15 | 2.02 | 2.02 | |
| 30 | 2.03 | 2.04 | |
| 45 | 2.04 | 2.02 | |
| 60 | 2.02 | 2.00 | No Reduction |

*FAC = Free Available Chlorine

The first set of data (Tests #1 and #2) use the low pH acidic composition made with electrolysis at a 1 ppm copper dosage and chlorine at 1 and 2 ppm. This data shows that there are no significant reductions in chlorine over the 1 hour test period. The second set of data (Tests #3 and #4) use the low pH acidic composition made without electrolysis at 1 ppm copper dosage and chlorine at 1 ppm and 2 ppm. This data again shows that there are no significant reductions in chlorine over the 1 hour test period.

These tests show that there is no incompatibility between the low pH acidic composition made with sodium sulfate and chlorine. Accordingly, the composition could be used in conjunction with chlorine as a disinfectant for food products or food processing equipment, for disinfecting water, or for treatment of waste water.

Example 6

Effect of Acidic Composition on Bacterial and Fungal Pathogens

The USP Challenge test (Protocol USP23), an accepted test showing the ability of a substance to retard the growth of tested pathogens, was performed to analyze the ability of an acidic composition, prepared according to Example 1 or 3 and containing sulfuric acid, ammonium sulfate, and copper sulfate at approximately 2-3 ppm, to destroy bacterial and fungal pathogens. Results are shown in Table III and demonstrate that the acidic composition destroyed all of the pathogens tested and growth did not recur during the 28 day testing period.

TABLE III

Challenge Test Results

| | Initial | Colony Forming Units/ml | | | |
|---|---|---|---|---|---|
| Microorganism | Inoculum/ml | Day 7 | Day 14 | Day 21 | Day 28 |
| A. niger | $1.9 \times 10^5$ | <10 | <10 | <10 | <10 |
| B. albicans | $2.2 \times 10^5$ | <10 | <10 | <10 | <10 |
| E. coli | $1.7 \times 10^5$ | <10 | <10 | <10 | <10 |
| P. aeruginosa | $3.5 \times 10^5$ | <10 | <10 | <10 | <10 |
| S. aureus | $2.4 \times 10^5$ | <10 | <10 | <10 | <10 |
| L. monocytoges | $1.8 \times 10^5$ | <10 | <10 | <10 | <10 |
| Salmonella/Shigella Mix | $1.5 \times 10^5$ | <10 | <10 | <10 | <10 |

The USP Zone of Inhibition test shows that a composition is effective at retarding the growth of pathogens if 1. The concentration of viable bacteria is reduced to not more than 0.1% of the initial concentration by day 14, 2. The concentration of viable yeast an mold remains at or below the initial concentration during the first 14 days, 3. The concentration of each test microorganism remains at or below these designated levels during the remainder of the 28 day test period, and 4. A clear zone of inhibition of a bacteria indicates properties similar to the antibiotic novobiotin and no bacterial growth.

As shown in Table IV, the acidic composition, prepared according to Example 1 or 3 and containing sulfuric acid, ammonium sulfate, and copper sulfate at approximately 2-3 ppm, meets all these criteria.

TABLE IV

Zone of Inhibition Test Results

| | Zone of Inhibition | | |
|---|---|---|---|
| Microorganism | Acidic Composition | Negative Control | Novobiotin |
| Staphylococcus aureus | 16.5 mm | No Zone | 27.8 mm |
| Bacillus albicans | 14.0 mm | No Zone | 27.8 mm |
| Escherichia coli | 13.8 mm | No Zone | 27.8 mm |
| Pseudomonas aeroginosa | 8.2 mm | No Zone | 27.8 mm |
| Listeria monocytogens | 15.4 | No Zone | 27.8 mm |
| Salmonella/Shigella Mix | 14.7 mm | No Zone | 27.8 mm |
| Aspergillus albicans | 7.8 mm | No Zone | 27.8 mm |

The USP Log Reduction test analyzes the ability of a composition to kill pathogenic organisms in water. Sterile buffered water is used as a control. An acidic composition, prepared according to Example 1 or 3 and containing sulfuric acid, ammonium sulfate, and copper sulfate at approximately 2-3 ppm, is the "product" in Table V below. The acidic composition was added to the water to a concentration of approximately 1 ppm. The results of the Log Reduction test demonstrate that the acidic composition was capable of killing 50-100% of bacterial organisms in water within 5 to 15 minutes of treatment and 20% of the fungal pathogen in water within 15 minutes of treatment.

TABLE V

Log Reduction Test Results

| Exposure Time (Minutes) | Concentration of Organism (CFU/ml) Control | Concentration of Organism (CFU/ml) Product | % Reduction Control | % Reduction Product | Log Reduction Control | Log Reduction Product |
|---|---|---|---|---|---|---|
| *Escherichia colia* ATCC 8739 | | | | | | |
| Initial | $2.7 \times 10^5$ | $2.7 \times 10^5$ | — | — | — | — |
| 01 | $2.7 \times 10^5$ | $1.3 \times 10^5$ | 0.0 | 18.5 | 0.0 | 0.3 |
| 05 | $2.6 \times 10^5$ | $7.5 \times 10^4$ | 3.7 | 37.0 | 0.0 | 0.9 |
| 15 | $2.7 \times 10^5$ | $2.3 \times 10^5$ | 0.0 | 51.9 | 0.0 | 1.0 |
| *Pseudomonas aeruginosa* ATCC 9027 | | | | | | |
| Initial | $2.2 \times 10^5$ | $2.1 \times 10^5$ | — | — | — | — |
| 01 | $2.2 \times 10^5$ | $1.7 \times 10^5$ | 0.0 | 22.7 | 0.0 | 0.3 |
| 05 | $2.2 \times 10^5$ | $1.2 \times 10^5$ | 0.0 | 45.4 | 0.0 | 0.6 |
| 05 | $2.2 \times 10^5$ | $9.4 \times 10^4$ | 0.0 | 57.3 | 0.0 | 0.7 |
| *Staphylococcus aureus* ATCC 6538 | | | | | | |
| Initial | $1.9 \times 10^5$ | $1.9 \times 10^5$ | — | — | — | — |
| 01 | $1.9 \times 10^5$ | $1.2 \times 10^5$ | 0.0 | 36.8 | 0.0 | 0.3 |
| 05 | $1.9 \times 10^5$ | $8.9 \times 10^4$ | 0.0 | 53.2 | 0.0 | 0.4 |
| 15 | $1.9 \times 10^5$ | $3.2 \times 10^4$ | 0.0 | 83.2 | 0.0 | 0.9 |
| *Aspergillus niger* | | | | | | |
| Initial | $1.8 \times 10^5$ | $1.8 \times 10^5$ | — | — | — | — |
| 01 | $1.8 \times 10^5$ | $1.7 \times 10^5$ | 0.0 | 5.9 | 0.0 | 0.1 |
| 05 | $1.7 \times 10^5$ | $1.5 \times 10^5$ | 5.9 | 11.8 | 0.1 | 0.2 |
| 15 | $1.8 \times 10^5$ | $1.4 \times 10^5$ | 0.0 | 22.2 | 0.0 | 0.3 |
| *Bacillus albicans* | | | | | | |
| Initial | $2.7 \times 10^5$ | $2.7 \times 10^5$ | — | — | — | — |
| 01 | $2.7 \times 10^5$ | $1.6 \times 10^5$ | 0.0 | 40.7 | 0.0 | 0.4 |
| 05 | $2.7 \times 10^5$ | $9.4 \times 10^4$ | 0.0 | 65.2 | 0.0 | 0.6 |
| 15 | $2.7 \times 10^5$ | $1.2 \times 10^4$ | 0.0 | 95.6 | 0.0 | 0.9 |
| *Listeria monocytogenes* | | | | | | |
| Initial | $1.6 \times 10^5$ | $1.6 \times 10^5$ | — | — | — | — |
| 01 | $1.5 \times 10^5$ | $9.1 \times 10^4$ | -5.9 | 46.5 | -0.1 | 0.4 |
| 05 | $1.6 \times 10^5$ | $7.2 \times 10^3$ | 0.0 | 95.5 | 0.0 | 0.9 |
| 15 | $1.6 \times 10^5$ | $5.8 \times 10^2$ | 0.0 | 99.6 | 0.0 | 1.0 |
| *Salmonella/Shigella* Strain A | | | | | | |
| Initial | $1.2 \times 10^5$ | $1.2 \times 10^5$ | — | — | — | — |
| 01 | $1.2 \times 10^5$ | $7.2 \times 10^4$ | 0.0 | 40.0 | 0.0 | 0.4 |
| 05 | $1.3 \times 10^5$ | $9.3 \times 10^3$ | -8.3 | 92.8 | -0.1 | 0.9 |
| 15 | $1.1 \times 10^5$ | $2.8 \times 10^2$ | 8.3 | 99.7 | 0.1 | 1.0 |

Example 7

Treatment of Tomatoes and Melons with Acidic Composition Prepared with Ammonium Sulfate The composition described in Example 6 was tested on tomatoes and honey dew melons. Tomatoes were sliced and inoculated with *Salmonella choleraesuis* (Log 10 CFU/ml). Inoculated tomatoes were sprayed or submerged in an approximately 1:2000 dilution of the acidic composition then tested for *S. choleraesuis* at 1, 5, and 10 minutes. Control tomatoes were sliced and inoculated, but not further treated. Results are shown in FIG. 1. Both spraying and submerging the tomatoes in the composition greatly reduced the amount of *S. choleraesuis* on the fruit.

Figure 2:
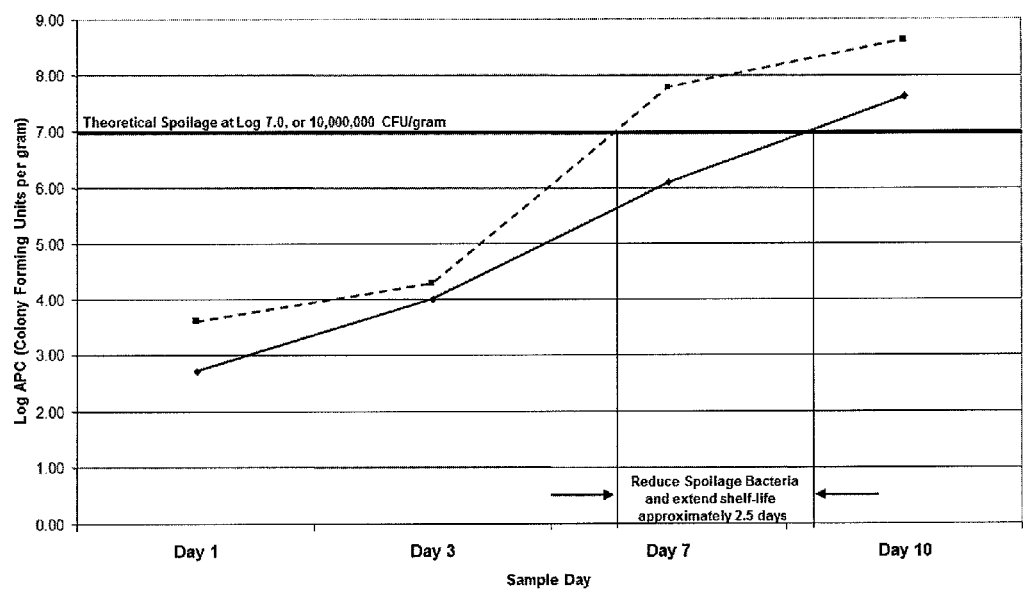
FIG. 2 is a graph showing the effects of the acidic composition described in Example 7 on the presence of bacteria in honey dew melons. Solid line—treated fruit; Dashed line—control fruit.

Honey dew melons were sliced and either sprayed or submerged in the composition and APC tested 2, 6, and 9 days thereafter. Control melons were sliced and inoculated, but not further treated. The results, shown in FIG. 2, demonstrate that treatment with the composition inhibited bacterial growth and extended shelf-life of the fruit for approximately 2.5 days.

Example 8

Treatment of Fresh Produce with Acidic Composition Prepared with Sodium Sulfate

An acidic composition was prepared as described in Example 5 with sulfuric acid and sodium sulfate and diluted 1:2000 in water. Copper sulfate was added to approximately 2-3 ppm, and sodium hypochlorite was added to less than 1 ppm. The final composition was tested as a produce wash to remove microorganisms from produce. Produce was treated by either spraying or submerging in the final composition. Bacterial and fungal colony forming units were analyzed six days after treatment. Control produce was treated with water containing 50 ppm sodium hypochlorite. The results of tests on lettuce, shown in Tables VI and VII below, demonstrate that the acidic composition is effective at destroying bacterial and fungal pathogens on fresh produce.

TABLE VI

Effect of composition on lettuce samples

| Microscopic Exam | Treated sample | Treated sample |
|---|---|---|
| Aerobic Plate Count, cfu/g | 6000 | 14,500 |
| Total Coliforms, cfu/g | None Detected | None Detected |
| *Staphylococcus*, cfu/g | ≤2 | ≤2 |
| *Salmonella/Shigella*, cfu/g | None Detected | None Detected |
| Yeast, cfu/g | None Detected | None Detected |
| Mold, cfu/g | 1 | 1 |
| | Control sample | Control sample |
| Aerobic Plate Count, cfu/g | 45,500 | 31,000 |
| Total Coliforms, cfu/g | 14 | None Detected |
| *Staphylococcus*, cfu/g | 11 | 2 |
| *Salmonella/Shigella*, cfu/g | None Detected | None Detected |
| Yeast, cfu/g | 4 | 3 |
| Mold, cfu/g | 7 | 8 |
| Microscopic Exam | Control Sample | Treated Sample |
| Aerobic Plate Count, cfu/g | 37000 | 200 |
| Fecal Coliforms, cfu/g | ≥1600 | ≤2 |
| *E. coli*, cfu/g | 96 | ≤2 |
| *Staphylococcus*, cfu/g | 10 | None Detected |
| *Salmonella/Shigella*, cfu/25 g | 1 | None Detected |
| Yeast, cfu/g | 45 | 30 |

TABLE VII

Effect of composition on different types of lettuce

| | Control (Chlorine) | Treated |
|---|---|---|
| ROMAINE HEARTS LETTUCE | | |
| Aerobic Heterophilic (TPC), cfu/g | 170,000 | 94% reduction |
| Fecal Coliforms, cfu/g | 50 | 13 |
| *E. coli*, cfu/g | 13 | None Detected |
| *Staphylococcus*, cfu/g | None Detected | None Detected |
| Pathogens as *Salmonella/Shigella*, cfu/g | None Detected | None Detected |
| GREEN LEAF LETTUCE | | |
| Aerobic Heterophilic (TPC), cfu/g | 1,280,000 | 99% reduction |
| Fecal Coliforms, cfu/g | ≥1600 | None Detected |
| *E. coli*, cfu/g | 53 | None Detected |
| *Staphylococcus*, cfu/g | 80 | None Detected |
| Pathogens as *Salmonella/Shigella*, cfu/g | 4 | None Detected |
| ICEBERG LETTUCE | | |
| Aerobic Heterophilic (TPC), cfu/g | 600,000 | 93% reduction |

TABLE VII-continued

Effect of composition on different types of lettuce

| | Control (Chlorine) | Treated |
|---|---|---|
| Fecal Coliforms, cfu/g | ≥1600 | 13 |
| *E. coli*, cfu/g | 93 | 2 |
| *Staphylococcus*, cfu/g | 23 | 2 |
| Pathogens as *Salmonella/Shigella*, cfu/g | None Detected | None Detected |

We claim:

1. A method for destroying microorganisms on a food product, food processing equipment, or in an aqueous solution comprising applying to the food product, food processing equipment, or aqueous solution a composition that is not an irritant, or a dilution thereof, prepared by the steps comprising
    a) combining a low pH acid of approximately 98% purity, selected from the group consisting of sulfuric acid, phosphoric acid, fumaric acid and acetic acid, with water and a metal sulfate to provide a mixture;
    b) heating the mixture of step a) in a pressurized vessel at approximately 15 psi at a temperature between about 250° F. and about 1200° F.
    c) cooling the mixture of step b);
    d) adding a stabilizer at about 10 percent of the total weight of the mixture of step c) to the mixture after cooling, wherein the stabilizer comprises the mixture of step a); and
    e) adding sodium hypochlorite to the mixture.

2. The method of claim 1, wherein the food product is a fruit, flower, leaf, stem, root, seed or other edible part of a plant.

3. The method of claim 1, wherein the food product is a fungus.

4. The method of claim 1, wherein the microorganism is a bacterium, fungus, or virus.

5. The method of claim 1, wherein the metal sulfate is sodium sulfate.

6. The method of claim 1, further comprising adding a metal ion in the form of a metal sulfate to the composition or a dilution thereof.

7. The method of claim 6, wherein the metal sulfate is selected from the group consisting of copper sulfate, silver sulfate, zinc sulfate, magnesium sulfate, and manganese sulfate.

8. The method of claim 1, wherein the aqueous solution is waste water.

9. A method of making a composition, wherein the composition is not an irritant and wherein the composition is capable of destroying microorganisms when the composition is applied to a food or to a food processing equipment or to an aqueous solution and the microorganisms are contacted by the composition, comprising
    a) reacting an acid of approximately 98% purity, selected from the group consisting of sulfuric acid, phosphoric acid, fumaric acid and acetic acid, with water and at least one metal sulfate at a temperature between about 250° F. and about 1200° F. at a pressure of approximately 15 psi to provide a mixture;
    b) cooling the mixture to about 70° F. to about 160° F.;
    c) adding a stabilizer at about 10 percent of the total weight of the mixture of step b) to the mixture after cooling, wherein the stabilizer comprises the mixture of step a); and
    d) adding sodium hypochlorite to the mixture of step c).

10. The method of claim 9, wherein the at least one metal sulfate is sodium sulfate.

11. The method of claim 9, further comprising adding an additional metal ion in the form of a metal sulfate to the composition or a dilution thereof.

12. The method of claim 9, wherein the metal sulfate is selected from the group consisting of copper sulfate, silver sulfate, zinc sulfate, magnesium sulfate, and manganese sulfate.

13. The method of claim 9, wherein the food product is a fruit, flower, leaf, stem, root, seed or other edible part of a plant.

14. The method of claim 9, wherein the food product is a fungus.

15. The method of claim 9, wherein the microorganism is a bacterium, fungus, or virus.

* * * * *